United States Patent [19]
Adkins et al.

[11] Patent Number: 5,914,409
[45] Date of Patent: Jun. 22, 1999

[54] TOLYLTRIAZOLE PROCESS

[75] Inventors: Rick L. Adkins, New Martinsville, W. Va.; Craig M. Young, Summerville, S.C.

[73] Assignee: Bayer Corporation, Pittsburgh, Pa.

[21] Appl. No.: 09/030,790

[22] Filed: Feb. 25, 1998

[51] Int. Cl.[6] .................................................. C07D 249/18
[52] U.S. Cl. .......................................................... 548/257
[58] Field of Search ............................................. 548/257

[56] References Cited

U.S. PATENT DOCUMENTS

| | | | |
|---|---|---|---|
| 2,861,076 | 11/1958 | Knott et al. | 260/288 |
| 3,227,726 | 1/1966 | Levy | 260/308 |
| 3,564,001 | 2/1971 | Long III | 260/308 |
| 3,637,514 | 1/1972 | Spatz et al. | 252/182 |
| 3,639,431 | 2/1972 | McTeer et al. | 252/390 |
| 3,732,239 | 5/1973 | Spatz et al. | 260/308 B |
| 3,970,667 | 7/1976 | Gengnagel et al. | 260/308 B |
| 4,158,660 | 6/1979 | Gavin et al. | 260/308 B |
| 4,170,521 | 10/1979 | Carr | 203/6 |
| 4,363,914 | 12/1982 | Long et al. | 548/257 |
| 4,424,360 | 1/1984 | Hagedorn et al. | 548/257 |
| 4,439,361 | 3/1984 | Karrenbauer et al. | 260/141 |
| 4,528,381 | 7/1985 | Gencarelli et al. | 548/257 |
| 4,549,026 | 10/1985 | Deur et al. | 548/257 |
| 4,918,195 | 4/1990 | Schnegg et al. | 548/257 |

FOREIGN PATENT DOCUMENTS 1581407   12/1980   United Kingdom.

*Primary Examiner*—Patricia L. Morris
*Attorney, Agent, or Firm*—Joseph C. Gil; N. Denise Brown

[57] ABSTRACT

This invention relates to an improved process for the production of tolyltriazole in which the tolyltriazole is a lighter colored product. The color improvement in the tolyltriazole produced from this process occurs when the ortho-toluenediamine reactant is previously stabilized by treatment with a compound selected from the group consisting of aldehydes, ketones, acetals and ketals. The process of the present invention reduces the need to purify (by, for example, filtration or distillation) the tolyltriazole prior to being used commercially.

19 Claims, No Drawings

TOLYLTRIAZOLE PROCESS

BACKGROUND OF THE INVENTION

This invention relates to an improved process for the production of tolyltriazole in which the tolyltriazole is a lighter colored product. The color improvement in the tolyltriazole produced from this process occurs when the ortho-toluenediamine reactant is previously stabilized by treatment with a compound selected from the group consisting of aldehydes, ketones, acetals and ketals. The process of the present invention reduces the need to filter (or distill) the tolyltriazole prior to being used commercially.

Processes for the production of tolyltriazoles and benzotriazoles are known and described in, for example, U.S. Pat. Nos. 2,861,076, 3,227,726, 3,564,001, 3,637,514, 3,639,431, 3,732,239, 3,970,667, 4,158,660, 4,363,914, 4,424,360, 4,439,361, 4,528,381, 4,549,026 and 4,918,195, and GB Patent 1,581,407. Solid tolyltriazoles are formed in some of these processes and liquid tolyltriazoles are formed in others.

Tolyltriazoles are known to be useful as corrosion inhibitors, particularly for copper surfaces, synthetic detergents and antifreezes, as UV stabilizers, as intermediates in numerous syntheses such as, for example, dyes, and in water treatment applications. Typically, however, for these tolyltriazoles to be suitable for certain applications, it is necessary for the tolyltriazole to be of considerably high purity. Discoloration inherently occurs during the processes for producing tolyltriazole due to chemical oxidation of compounds such as, for example, ortho-toluenediamine. Therefore, it is usually necessary to purify tolyltriazoles.

Suitable processes known for purifying tolyltriazoles and benzotriazoles are known and described in, for example, U.S. Pat. Nos. 3,732,239, 3,970,667, 4,528,381 and 4,918,195, and in GB Patent 1,581,407. When crude diaminotoluene is used as the reactant before starting diazotization and ring closure reaction, U.S. Pat. No. 3,732,239 discloses that it is necessary to subject the produced tolyltriazoles to an expensive purification via distillation. As described in U.S. Pat. No. 3,970,667, the reaction mixture containing triazole (with no intermediate isolation of tolyltriazole) can be made alkaline using aqueous sodium hydroxide solution and being subjected to several clarifying filtrations, and once the mixture is made again acidified via nitric acid, the precipitated triazole can be isolated. GB Patent 1,581,407 discloses that once volatile components are distilled off the reaction mixture, the mixture is inoculated and the triazole is recovered by crystallization.

It has also been attempted, following the diazotization with sodium nitrate in a water/acetic acid reaction medium, to first separate off the benzotriazole as an oil, wash it with water, and to distill the benzotriazole under reduced pressure. This simple vacuum distillation was not completely satisfactory though, as U.S. Pat. No. 4,170,521 discloses the vacuum distillation of benzotriazole in the presence of a small amount of formaldehyde.

U.S. Pat. No. 4,528,381 further discloses that these distillations did not provide fused triazoles of sufficient purity and color stability. It is described in this reference that to avoid unsatisfactory distillation, the fused triazoles are reacted with alkyl nitrites in the presence of alkanols ($C_6$ to $C_{10}$ alkanols) as the reaction medium. The resultant triazole is then extracted from this reaction medium by means of aqueous sodium hydroxide solution.

Although progress has been made in the area of purifying tolyltriazoles, the need for additional improvements still exists. Methods to purify tolyltriazoles which are easier, less time consuming and/or more economical than those currently known and presently being used are of interest and important in this field of chemistry.

It has now been found that a high purity tolyltriazole can be readily produced by conventional diazotization processes of ortho-toluenediamine with a nitrite, if the ortho-toluenediamine has first been stabilized against discoloration by the addition of a small quantity of certain types of compounds. This process reduces or possibly eliminates the need for the prepared tolyltriazoles to be further purified prior to being used.

Advantages of the present invention include the fact that it is not necessary to modify the existing tolyltriazole process equipment to install purification steps. The tolyltriazole produced by the present invention will require less decolorization. Also, since this invention modifies the raw material (i.e., o-TDA) used as a reactant in the process and not the actual tolyltriazole process, this results in a substantial cost savings due to decreased processing requirements.

SUMMARY OF THE INVENTION

This invention relates to an improved process for the production of tolyltriazole in which the tolyltriazole produced is a lighter color than tolyltriazole produced by conventional processes. This invention also relates to the tolyltriazole produced by the process of this invention.

The process of the invention for producing tolyltriazole comprises diazotizing ortho-toluenediamine with a nitrite, wherein said ortho-toluenediamine comprises from 0.001 to 5% by weight, based on 100% by weight of ortho-toluenediamine, of a compound selected from the group consisting of aldehydes, ketones, acetals and ketals. The tolyltriazole produced by this process exhibits lower absorbencies when analyzed by UV/V is spectrophotometry.

This process may be run at relatively low temperatures or at relatively high temperatures. Depending on the temperature during the process, an additional step to close the ring may be necessary. Typically, when the process temperature is less than about 10° C., ring closure by cyclization is necessary. In processes where the temperature is greater than 10° C., preferably greater than about 50° C., ring closure naturally occurs.

The tolyltriazoles of the present invention can be solid products or liquid products. In the process for producing both the solid and the liquid products, ortho-toluenediamine is diazotized with a nitrite. Suitable processes for the present invention include both batch and continuous processes. Specific details concerning batch processes are as described in, for example, U.S. Pat. No. 3,227,726, the disclosure of which is herein incorporated by reference.

Continuous processes for the production of tolyltriazoles require the addition of the nitrite, ortho-toluenediamine and the reaction medium with mixing at a controlled temperature, thus forming the tolyltriazole oil. The organic phase containing the tolyltriazole oil is then separated from the water phase, washed with water and then neutralized by adding a basic solution. This solution is filtered through activated carbon, if necessary, to remove any additional color impurities. After this, the excess water is removed by suitable means such as, for example, evaporation, to form a concentrated solution of the tolyltriazole salt. Specific details for continuous processes are as described in, for example, U.S. Pat. Nos. 3,227,726 and 3,564,001, the disclosures of which are herein incorporated by reference.

Various processes for the production of solid tolyltriazoles are known and described in the art. Some of the known processes by which solid tolyltriazole can be produced include those which are described in, for example, U.S. Pat. Nos. 4,424,360, 4,528,381 and 4,918,195, the disclosures of which are herein incorporated by reference, and British Patent GB 1,581,407, the disclosure of which are herein incorporated by reference.

Processes for the production of liquid tolyltriazoles are also known and described in the art. Some examples of suitable processes for the present invention include those set forth in, for example, U.S. Pat. No. 4,363,914, the disclosure of which is herein incorporated by reference. When liquid tolyltriazoles are produced, these are generally in the form of the alkali metal salt. Liquid tolyltriazoles are preferred in the present invention.

In general, liquid tolyltriazoles are produced by diazotization of ortho-toluenediamine with a nitrite such as, for example, an alkali metal nitrite, in the presence of a suitable acid. Once the resultant solution phase separates, the organic layer can be washed with water, and neutralized by adding a basic solution to increase the pH. A basic solution such as, for example aqueous sodium hydroxide (NaOH), is added until a pH greater than 7, preferably greater than 10, more preferably greater than 11 and most preferably from 11 to 12 is achieved. The solution is then filtered through an activated filtrate such as, for example, activated carbon to purify the product.

In the process of the present invention, it is first necessary to stabilize the ortho-toluenediamine against air oxidation by first treating it with a compound selected from the group consisting of aldehydes, ketones, acetal and mixtures thereof. This requires the addition of from 0.001 to 5% by weight, preferably 0.01 to 2%, and more preferably 0.1 to 0.5%, based on 100% by weight of the ortho-toluenediamine, of at least one of these compounds to ortho-toluenediamine.

As used in the present invention, the term stable with respect to the ortho-toluenediamine compositions of the present invention means that the color of these is lighter than the standard when stored at a temperature of $\geq 25°$ C. The standard is the corresponding untreated ortho-toluenediamine. In accordance with the present invention, suitable compounds for treating the ortho-toluenediamines to prevent discoloration are selected from the group consisting of aldehydes, ketones, acetals, ketals and mixtures thereof. Suitable compounds can be aliphatic (i.e., cyclic or acyclic), or aromatic (including benzylic). Some examples of such compounds include formaldehyde, paraformaldehyde, trioxane, acetaldehyde, butyraldehyde, glutaraldehyde, benzaldehyde, acetone, dimethoxymethane, salicylaldehyde, glyoxal, methyldehyde, propionaldehyde, 2-methylpropanal, pentanal, 3-methylbutanal, hexanal, heptanal, octanal, phenylacetaldehyde, o-tolualdehyde, p-tolualdehyde, p-hydroxybenzaldehyde, p-methoxybenzaldehyde, methyl alkyl ketones such as, for example, methyl ethyl ketone, methyl propyl ketone, methyl isopropyl ketone, methyl isobutyl ketone, methyl sec-butyl ketone, methyl hexyl ketone, etc., dialkyl ketones such as, for example, diethyl ketone, diisopropyl ketone, diisobutyl ketone, ethyl propyl ketone, butyl ethyl ketone, ethyl amyl ketone, etc., unsaturated ketones such as, for example, methyl vinyl ketones, methyl isopropenyl ketone, mesityl oxide, isomesityl oxide, etc., diketones such as, for example, 2,3-butanedione, 2,3-pentanedione, 2,5-hexanedione, etc., cyclic ketones including, for example, cyclopentanone, cyclohexanone, cyclopentanone, 3,3,5-trimethylcyclohexanone, etc., aromatic ketones such as, for example, acetophenone, benzophenone, propiophenone, etc.

Other suitable acetals and ketals include, for example, 1,1-dimethoxyethane, triethyl orthoformate, triethyl orthoacetate, 1,3-dioxolane, 2-methyl-1,3-dioxolane, 1,3-dioxane, 2,2-dimethyl-1,3-dioxolane, solketal, benzaldehyde dimethylacetal, etc.

It is preferred that this compound be selected from the group consisting of formaldehyde, paraformaldehyde, trioxane, acetaldehyde, butyraldehyde, glutaraldehyde, benzaldehyde, acetone and dimethoxymethane. Paraformaldehyde is a particularly preferred compound.

Aldehydes suitable for the present invention may be prepared by any of the known processes in the art. Examples of suitable processes are described in, for example, *Kirk-Othmer Encyclopedia of Chemical Technology*, Fourth Edition, Volume 1, pp. 932–933, the disclosure of which is herein incorporated by reference. Processes for preparing ketones suitable for the present invention include those described in, for example, *Kirk-Othmer Encyclopedia of Chemical Technology*, Fourth Edition, Volume 14, pp. 985–1012, the disclosure of which is herein incorporated by reference. Suitable processes for preparing suitable acetals and ketals for the present invention are disclosed in, for example, *Advanced Organic Chemistry*, Second Edition, by Jerry March, 1977, pp. 810–812, the disclosure of which is herein incorporated by reference.

Suitable nitrites to be used in the diazotization of ortho-toluenediamine include, for example, alkali metal nitrites, alkyl nitrites, etc. Suitable alkyl nitrites include those compounds which have, for example, from 1 up to about 10 carbon atoms (inclusive), preferably 1 to 5 carbon atoms, and most preferably 1 carbon atom. Some examples include methyl nitrite, ethyl nitrite, propyl nitrite, isopropyl nitrite, butyl nitrite, isobutyl nitrite, amyl nitrite, isoamyl nitrite, hexyl nitrite, 2-ethylhexyl nitrite, octyl nitrite, decyl nitrite, benzyl nitrite, nitrites of polyalcohols such as, for example, ethylene glycol, polyethylene glycol, polyvinyl alcohol, etc. Preferred alkyl nitrites are methyl nitrite, ethyl nitrite, propyl nitrite and butyl nitrite.

Suitable examples of alkali metal nitrites include compounds such as sodium nitrite, potassium nitrite, lithium nitrite, cesium nitrite, etc. Preferred alkali metal nitrites are sodium nitrite and potassium nitrite.

The ortho-toluenediamine and the nitrite compound are present in quantities such that the molar ratio of amine to nitrite is from about 1:0.8 to about 1:1.5, preferably from about 1:0.9 to about 1:1.1.

When using alkali metal nitrites, the reaction medium can be aqueous or anhydrous forms of the following: an organic acid, a mineral acid or an organic medium. Suitable aqueous medium include, for example, carboxylic acids such as, for example, formic acid, acetic acid, propionic acid, butyric acid, oxalic acid, adipic acid, benzoic acid, phthalic acid, inorganic acids such as, for example, sulfuric acid, phosphoric acid, hydrochloric acid, alkali or alkaline earth metal bisulfates such as, for example, sodium bisulfate and potassium bisulfate, etc. Other suitable reaction medium include those as described in U.S. Pat. No. 2,861,076 at column 3, lines 45ff, the disclosure of which is herein incorporated by reference. Preferred reaction medium for the alkali metal nitrites are as aqueous solutions.

When using alkyl nitrites in the present invention, suitable organic medium including compounds such as, for example, alcohols, glycols, glycol ethers, aromatic hydrocarbons, and chlorinated aromatic hydrocarbons may be used. Examples of suitable solvents include compounds such as benzene, chlorobenzene, o-dichlorobenzene, toluene, ethyl benzene, isopropyl benzene, xylene, tetraline, pentane, hexane, cyclohexane, decane, pentadecane, chlorinated hydrocarbons such as dichloroethane, carbon tetrachloride, trichloroethane, isobutyl chloride, ethanol, propanol, ethylene glycol, methyl ether, ethyl ether, etc. Preferred organic solvents include alcohols containing from 1 to 6 carbon atoms, preferably 1 to 3 carbon atoms, and most preferably 1 carbon atom. Some examples include methanol, ethanol, propanol, isopropanol, butanol, isobutanol, amyl alcohol, hexanol, etc. It is also possible for the solvents or diluents for the process according to the invention to contain water in an amount of up to a maximum of 40% in general. Methanol, water-containing methanol, ethanol, isopropanol, toluene, chlorobenzene, o-dichlorobenzene and xylene are preferred solvents or diluents for the process according to the present invention.

Suitable catalysts which may optionally be used in the present invention include catalysts such as, for example, fused 1,2,3-triazole as described in, for example, U.S. Pat. No. 4,424,360, the disclosure of which is herein incorporated by reference. Useful levels of catalysts typically range from about 0.5 to about 5% by weight, based on the weight of the ortho-toluenediamine.

Suitable basic compositions to be added in the process of producing tolyltriazole salt of the present invention from an alkali metal nitrite include compositions known to increase the pH of the solution containing the tolyltriazole. Compositions suitable to increase the pH include, for example, alkali compounds such as, for example, a 50% sodium hydroxide solution, potassium hydroxide solution, sodium carbonate, sodium bicarbonate, etc.

The quantity of basic compositions added to the reaction mixture is sufficient to obtain a pH of preferably from about 8 up to about 14, more preferably of from about 10 up to about 12. A pH of greater than 7 is necessary to form the tolyltriazole salt.

In accordance with the present invention, the reaction mixture formed which contains ortho-toluenediamine, the nitrite and the acid can be run through an activated filtrate to assist in purification of the final product. Suitable activated filtrates include activated carbon, charcoal, kieselguhr, sodium dithionite, silica, etc.

When the desired product is the free tolyltriazole, rather than the water soluble salt, the free triazole can be readily generated by the addition of a sufficient amount of acid to neutralize the basic salt. Typically a pH of less than 7 and especially less than about 6 is sufficient to generate the free triazole. It is preferred to use the less expensive mineral acids, especially sulfuric acid, to generate the free tolyltriazole. Once the pH has been adjusted to the acidic side, the free tolyltriazole can be separated by decantation or a by a separatory funnel or other methods known in the art.

Tolyltriazoles are typically commercially available in two forms, either as the pure (free) tolyltriazoles or as aqueous solutions of their soluble salts, such as the sodium salts. The process described herein works very well for the production of either commercial form, however, it is most especially suited for the preparation of the aqueous medium salt solution because this process reduces or possibly eliminates the need for this product to be further processed and/or purified. In addition, with the selection of proper reaction equipment which would allow rapid heating to the proper reaction temperatures, this process can be conveniently used as a continuous process for the production of tolyltriazoles.

When free tolyltriazole is the desired product, the reaction mixture can be conveniently worked up by acidifying the crude mixture to a pH of about 6 or less, separating the tolyltriazole oil from the water and then, if desired, purifying the recovered oil by any of the methods well known within the art, such as, for example, recrystalization.

The following examples further illustrate details for the processes of this invention, and the products of these processes. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all parts and percentages are parts by weight and percentages by weight, respectively.

EXAMPLES

Example 1A 100 g. of freshly distilled ortho-toluenediamine (o-TDA) were placed in a flask. To this, 0.25 g. of paraformaldehyde was added, followed by mixing thoroughly. The sample was sealed, and placed in a 100° C. oven. After 12 hours, this treated sample had a Gardner color of 11.

Example 1B

A sealed sample of 100 g. of untreated, freshly distilled ortho-toluenediamine was placed in a 100° C. oven. After 12 hours, the untreated sample had a Gardner color >18.

Example 2A

Into a 500-ml flask equipped with a stirrer and condenser (under nitrogen) were added 0.467 mole of the ortho-toluenediamine from Example 1A above and 0.496 mole of 40% sodium nitrite solution, followed by heating to 80° C. Glacial acetic acid (0.597 mol) was slowly added, while maintaining the temperature below 80° C. The solution was heated at 80° C. for one hour, then cooled to room temperature to allow phase separation. The organic layer was washed with water, and 50% sodium hydroxide was added to a pH of 12. The solution was filtered through activated carbon and analyzed by a UV/V is spectrophotometer (0.4% by weight in water). The product had an absorbance of 0.165 at 396 nm.

Example 2B

Into a 500-ml flask equipped with a stirrer and condenser (under nitrogen) were added 0.467 mole of the ortho-toluenediamine from Example 1 B above and 0.496 mole of 40% sodium nitrite solution, followed by heating to 80° C. Glacial acetic acid (0.597 mol) was slowly added, while maintaining the temperature below 80° C. The solution was heated at 80° C. for one hour, then cooled to room temperature to allow phase separation. The organic layer was washed with water, and 50% sodium hydroxide was added to a pH of 12. The solution was filtered through activated carbon and analyzed by a UV/V is spectrophotometer (0.4% by weight in water). This tolyltriazole solution had an absorbance of 0.412 at 396 nm.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In a process for the production of tolyltriazole comprising diazotizing ortho-toluenediamine with a nitrite, the improvement wherein said ortho-toluenediamine is treated by adding from 0.001 to 5% by weight, based on 100% by weight of ortho-toluenediamine, of a compound selected from the group consisting of aldehydes, ketones, acetals and ketals.

2. The process of claim 1, wherein said compound is selected from the group consisting of formaldehyde, paraformaldehyde, trioxane, acetaldehyde, butyraldehyde, glutaraldehyde, benzaldehyde, acetone, dimethoxymethane and mixtures thereof.

3. The process of claim 1, wherein the nitrite is selected from the group consisting of an alkali metal nitrite, an alkyl nitrite and a nitrite of a polyalcohol.

4. The process of claim 3, wherein said nitrite is selected from the group consisting of sodium nitrite, potassium nitrite, methyl nitrite, ethyl nitrite, propyl nitrite and butyl nitrite.

5. The process of claim 1, wherein the ortho-toluenediamine and nitrite are present in quantities such that the molar ratio of amine to nitrite is from about 1:0.8 to about 1:1.5.

6. The process of claim 5, wherein the molar ratio of amine to nitrite is from about 1:0.9 to about 1:1.1.

7. In a process for the production of a liquid tolyltriazole comprising diazotizing ortho-toluenediamine with an alkali metal nitrite, the improvement wherein said ortho-toluenediamine is treated by adding from 0.001 to 5% by weight, based on 100% by weight of ortho-toluenediamine, of a compound selected from the group consisting of aldehydes, ketones, acetals and ketals.

8. The process of claim 7, wherein the diazotization occurs in the presence of an acid.

9. The process of claim 7, wherein the alkali metal nitrite is selected from the group consisting of sodium nitrite and potassium nitrite.

10. The process of claim 7, wherein said compound is selected from the group consisting of formaldehyde, paraformaldehyde, trioxane, acetaldehyde, butyraldehyde, glutaraldehyde, benzaldehyde, acetone, dimethoxymethane and mixtures thereof.

11. In a process for the production of a solid tolyltriazole comprising diazotizing ortho-toluenediamine with a nitrite, the improvement wherein said ortho-toluenediamine is treated by adding from 0.001 to 5% by weight, based on 100% by weight of toluenediamine, of a compound selected from the group consisting of aldehydes, ketones, acetals and ketals.

12. The process of claim 11, wherein the nitrite is selected from the group consisting of an alkali metal nitrite, an alkyl nitrite and a nitrite of a polyalcohol.

13. The process of claim 12, wherein said nitrite is selected from the group consisting of sodium nitrite, potassium nitrite, methyl nitrite, ethyl nitrite, propyl nitrite and butyl nitrite.

14. The process of claim 11, wherein the ortho-toluenediamine and nitrite are present in quantities such that the molar ratio of amine to nitrite is from about 1:0.8 to about 1:1.5.

15. The process of claim 14, wherein the molar ratio of amine to nitrite is from about 1:0.9 to about 1:1.1.

16. The process of claim 12, wherein said compound is selected from the group consisting of formaldehyde, paraformaldehyde, trioxane, acetaldehyde, butyraldehyde, glutaraldehyde, benzaldehyde, acetone, dimethoxymethane and mixtures thereof.

17. The tolyltriazole produced by the process of claim 1.

18. The liquid tolyltriazole produced by the process of claim 7.

19. The solid tolyltriazole produced by the process of claim 11.

* * * * *